(12) United States Patent
Echtermeyer

(10) Patent No.: US 9,752,982 B2
(45) Date of Patent: Sep. 5, 2017

(54) PLASMONIC SENSOR DEVICE AND METHOD FOR SURFACE PLASMON RESONANCE SPECTROSCOPY

(71) Applicant: Robert Bosch GmbH, Stuttgart (DE)

(72) Inventor: Tim Echtermeyer, Pliezhausen-Ruebgarten (DE)

(73) Assignee: ROBERT BOSCH GMBH, Stuttgart (DE)

( * ) Notice: Subject to any disclaimer, the term of this patent is extended or adjusted under 35 U.S.C. 154(b) by 162 days.

(21) Appl. No.: 14/599,322

(22) Filed: Jan. 16, 2015

(65) Prior Publication Data

US 2015/0233823 A1  Aug. 20, 2015

(30) Foreign Application Priority Data

Feb. 17, 2014 (DE) .......................... 10 2014 202 844

(51) Int. Cl.
  *G01N 21/55*   (2014.01)
  *G01N 21/552*  (2014.01)
(52) U.S. Cl.
  CPC ......... *G01N 21/554* (2013.01); *G01N 21/553* (2013.01); *G01N 2201/06113* (2013.01)
(58) Field of Classification Search
  CPC .................................................. G01N 21/55
  USPC ........................................................ 356/445
  See application file for complete search history.

(56) References Cited

U.S. PATENT DOCUMENTS

| | | | | |
|---|---|---|---|---|
| 6,417,924 B1* | 7/2002 | Kimura | ............... | G01N 21/553 356/445 |
| 6,879,401 B2* | 4/2005 | Gedig | ............... | G01N 21/553 356/445 |
| 7,187,446 B2* | 3/2007 | Kimura | ............... | G01N 21/553 250/573 |
| 7,265,844 B2* | 9/2007 | Codner | ............... | G01N 21/553 356/445 |
| 8,415,611 B2* | 4/2013 | Amako | ............... | G01N 21/553 250/237 G |
| 8,587,786 B2* | 11/2013 | Zybin | ............... | G01N 15/1463 356/445 |
| 2003/0179379 A1* | 9/2003 | Gedig | ............... | G01N 21/553 356/445 |
| 2004/0201849 A1* | 10/2004 | Codner | ............... | G01N 21/553 356/445 |
| 2007/0139653 A1 | 6/2007 | Guan et al. | | |

* cited by examiner

*Primary Examiner* — Roy M Punnoose
(74) *Attorney, Agent, or Firm* — Norton Rose Fulbright US LLP; Gerard Messina

(57) ABSTRACT

A plasmonic sensor device includes a light source, configured to generate coherent light; a metallic film, at least partially covered on one side by analyte molecules; at least one micromirror that is rotatable about at least one axis of rotation, which is positioned and developed in such a way that the coherent light is able to be guided at an angle of incidence to one side of the metallic film, the angle of incidence being variable by the rotating of the at least one micromirror about the at least one axis of rotation; and a detector configured to determine the intensity of the light guided onto the metallic film and reflected again from there, as a function of the angle of incidence, the coherent light generated by the light source being in such a state that surface plasmons are excitable in the metallic film depending on the angle of incidence.

19 Claims, 3 Drawing Sheets

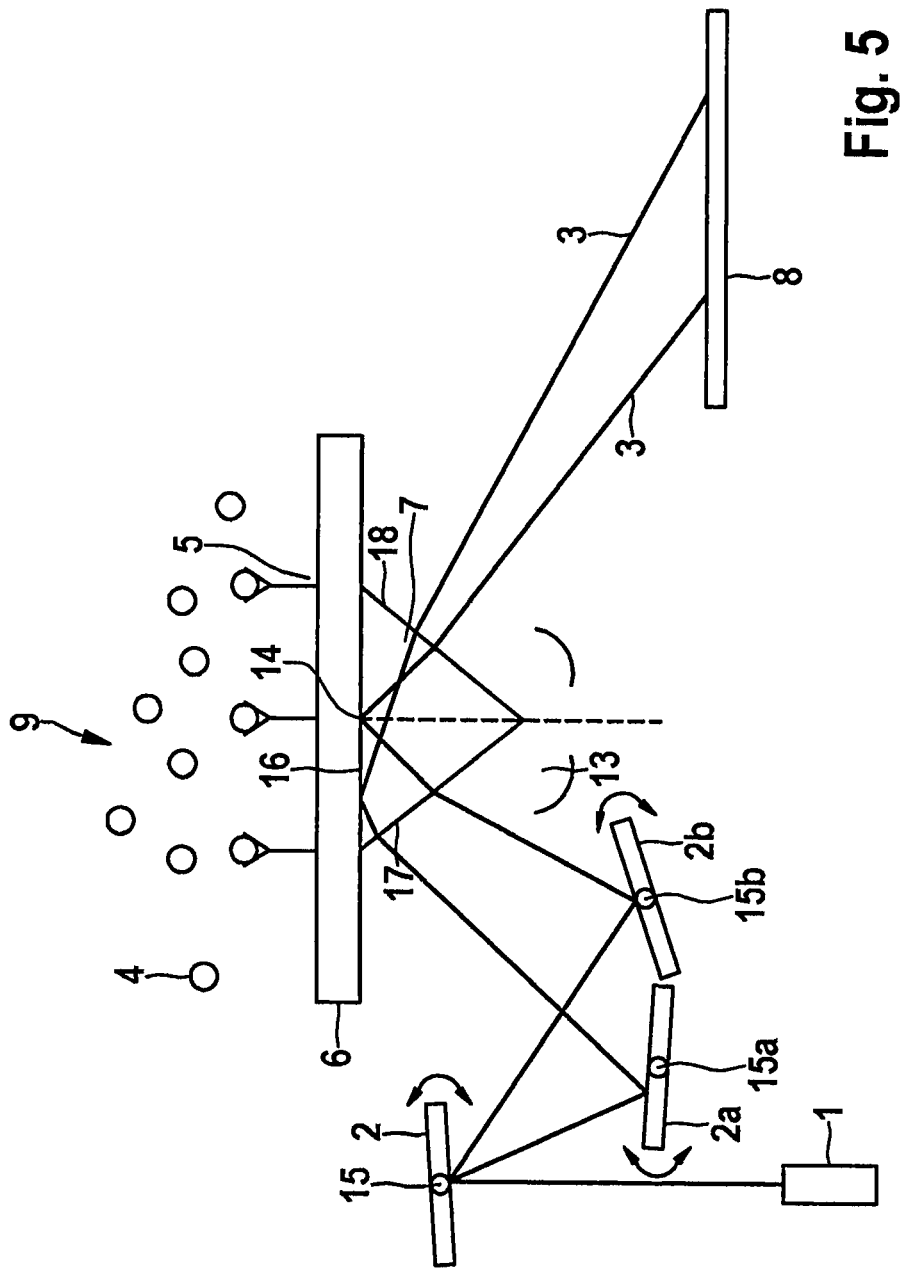

PLASMONIC SENSOR DEVICE AND METHOD FOR SURFACE PLASMON RESONANCE SPECTROSCOPY

FIELD OF THE INVENTION

The present invention relates to a plasmonic sensor device based on micromirrors and a method for surface plasmon resonance spectroscopy using such a sensor device.

BACKGROUND

Under certain conditions, if coherent light strikes an interface between a dielectric (such as air or glass) and a metallic film (such as gold), it is able to excite the conduction electrons near the metal surface to collective density fluctuations, so-called surface plasmons. In surface plasmon resonance spectroscopy (SPR spectroscopy), this effect is used, among other things, for investigating the adsorption and the properties of an analyte located on the metal surface. For this purpose, the intensity of the light reflected by the metal surface is determined as a function of the angle of incidence. The angle of incidence is varied in this case, for example, using a tiltable or rotatable mirror, via which the light is guided onto the metal surface. Based on the excitation of surface plasmons, an intensity minimum sets in at a certain angle of incidence. The associated angle of incidence depends particularly also on the condition of the analyte.

For a portable utilization of plasmonic analysis methods, a miniaturization of the needed mechanical and optical components is required. From European document EP 1 684 063 A1, a portable biochip scanner is known which includes an SPR unit that is present in the form of a rotating disk. Furthermore, from document US 2007/0139653 A1, a method is known in which a micromirror (MEMS) is used for an SPR-based biosensor. To vary the angle of incidence, a goniometer is used in this case, for example.

SUMMARY

For laboratory diagnostics close to the patient (POLT), however, a greatly miniaturized and closed-in-on-itself design is required which is, at the same time, simple to produce.

According to an example embodiment of the present invention, a plasmonic sensor device includes a light source that is developed to generate coherent light; a metallic film at least partially covered on one side by analyte molecules; at least one micromirror that is rotatable about at least one axis of rotation, and that is positioned and developed to guide coherent light at an angle of incidence to one side of the metallic film, the angle of incidence being variable by rotating the at least one micromirror about the at least one axis of rotation; and a detector that is developed to determine the intensity of the light guided onto the metallic film and reflected again from there, as a function of the angle of incidence; the coherent light generated by the light source being in such a state that surface plasmons are excitable in the metallic film depending on the angle of incidence.

According to an example embodiment of the present invention, a method for surface plasmon resonance spectroscopy using the example plasmonic sensor device includes the steps of varying the angle of incidence of coherent light onto metallic film by rotating the at least one micromirror, whereby, depending on the angle of incidence, surface plasmons are excited in the metallic film; and measuring the intensity of the coherent light guided onto the metallic film and reflected again from there, using the detector, as a function of the angle of incidence.

In an example embodiment, a miniaturized plasmonic sensor device is provided with the aid of at least one micromirror, which is rotatably supported in such a way that the angle of incidence of the light onto the metal surface is variable, without additional auxiliary means, such as a goniometer, being required. The intensity of the light reflected by the metal surface is measured in this case by a detector integrated into the sensor device, as a function of the angle of incidence.

A considerable advantage of the design approach according to the present invention is that the plasmonic sensor device is able to be executed in a greatly miniaturized manner. A micromirror is a so-called MEMS ("microelectromechanical system"), which has extensions in the micrometer range. The use of such micromirrors permits the dimensioning of the entire sensor device to be in the range of a few millimeters to centimeters. Both the light source and the detector can be integrated into such a sensor device.

In an example embodiment of the present invention, during the operation of the sensor device, the individual components can be fixed in their positions with respect to one another. The coherent light source, the metallic film, the detector and the at least one axis of rotation of the at least one micromirror are thus able to be provided in an immobile manner with respect to one another, so that the at least one micromirror is able to be rotated about its at least one axis of rotation. In this way, the plasmonic sensor device can advantageously be developed to be miniaturized, in a simple and cost-effective manner.

According to an example embodiment of the sensor device, the light source is able to generate a laser beam, which is then steered to the metallic film via the at least one micromirror. A laser beam is an advantageous coherent light source, which, in addition, is easy to handle, and is suitable for miniaturized built-on accessories.

According to an example embodiment of the present invention, the sensor device further includes a reflection prism, which can be positioned in such a way that its base area borders on the side of the metallic film facing away from the analyte molecules, and that the coherent light, coming from the light source, enters the reflection prism at an entry surface, is reflected at the boundary surface formed by the base area between the reflection prism and the metallic film, and exits again at an exit surface from the reflection prism before striking the detector.

In its basic design, this arrangement of the reflection prism corresponds to the so-called Kretschmann Configuration, which is used in many practical applications of surface plasmon resonance spectroscopy. In this case, the reflection prism is used for connecting the coherent light to the surface plasmons.

According to an example embodiment of the present invention, one side of the metallic film of the sensor device is developed as lattice structure positioned in such a way that the coherent light is able to be reflected at it before it strikes the detector. The lattice structure is an alternative possibility for coupling the wave vectors of light and surface plasmons. It requires no reflection prism and is thus advantageously simpler and able to be produced at smaller dimensions.

According to an example embodiment, the metallic film of the sensor device is provided with linkers via which the analyte molecules can couple with the metallic film, so that the excitation conditions for surface plasmons change in response to reactions between linkers and fitting analyte molecules. Linkers are advantageously an auxiliary way to couple the selected analyte to the metallic film.

According to an example embodiment, the detector of the sensor device is a CCD sensor or a CMOS sensor. Both sensor technologies are advantageous for the miniaturized operation and cost-effective to prepare. The expansion of the active surface of such a detector can advantageously be selected to be large enough so that a variation of the location of incidence brought about simultaneously by a variation in the angle of incidence can be compensated for by integrating the impinging quantity of light over the whole active surface. Conditioned upon this, the detector measures the intensity of the light exclusively as a function of the angle of incidence.

According to example embodiment, the metallic film of the sensor device includes gold and/or silver, which have particularly advantageous properties for the plasmonic system because of their conductivity and easy processability. Alternatively, however, other suitable metals can be provided, such as copper or titanium.

According to an example embodiment of the sensor device, the metallic film can be scanned two-dimensionally by the light, by the rotation of the at least one micromirror. Furthermore, in an example embodiment, the metallic film is developed as a test strip on which analyte areas of analyte molecules can be disposed next to one another. This advantageous specific embodiment permits one to design the plasmonic sensor device as a diagnostic device, similar to a conventional point-of-care test (POCT), such as a blood sugar measuring unit. The light source, the micromirror and the detector can be firmly integrated into the unit, while the test strip (such as a gold film) is introduced into the unit after the application of a substance that is to be analyzed, and removed again after the test. Because of the two-dimensional scannability of the test strip, it can be equipped with various linkers, so that testing can be done for different substances. Furthermore, this specific embodiment permits providing the test strip with reference structures, for example, which can be used for an automatic position correction of the test strip with respect to the other components. Alternatively, reserved areas can be provided on the test strip for reference measurements.

According to an example embodiment, the sensor device includes at least one additional micromirror that is rotatable about at least one additional axis of rotation. This at least one additional micromirror can be positioned and developed in such a way that the coherent light from the light source is able to be guided, using multiple reflections at the micromirrors, at an angle of incidence to a location of incidence on one side of the metallic film. The angle of incidence and the location of incidence can be varied, in this case, by the individual rotations of the micromirrors about the axes of rotation. This multi-mirror configuration advantageously creates additional degrees of freedom with respect to the manipulation of the angle of incidence and the location of incidence compared to an embodiment that includes only one micromirror with only one axis of rotation. The various axes of rotation, in particular, need not be disposed in parallel to one another.

According to an example embodiment, the method for surface plasmon resonance spectroscopy further includes scanning of the metallic film by varying the location of incidence of the coherent light by the rotation of the at least one micromirror.

Additional features and advantages of the present invention are explained below on the basis of specific embodiments and with reference to the figures.

BRIEF DESCRIPTION OF THE DRAWINGS

FIG. 5 is a schematic cross section of a plasmonic sensor device with reflection prisms and three micromirrors according to another example embodiment of the present invention.

DETAILED DESCRIPTION

In the figures, identical reference symbols denote identical or functionally equivalent elements.

Figure 1:
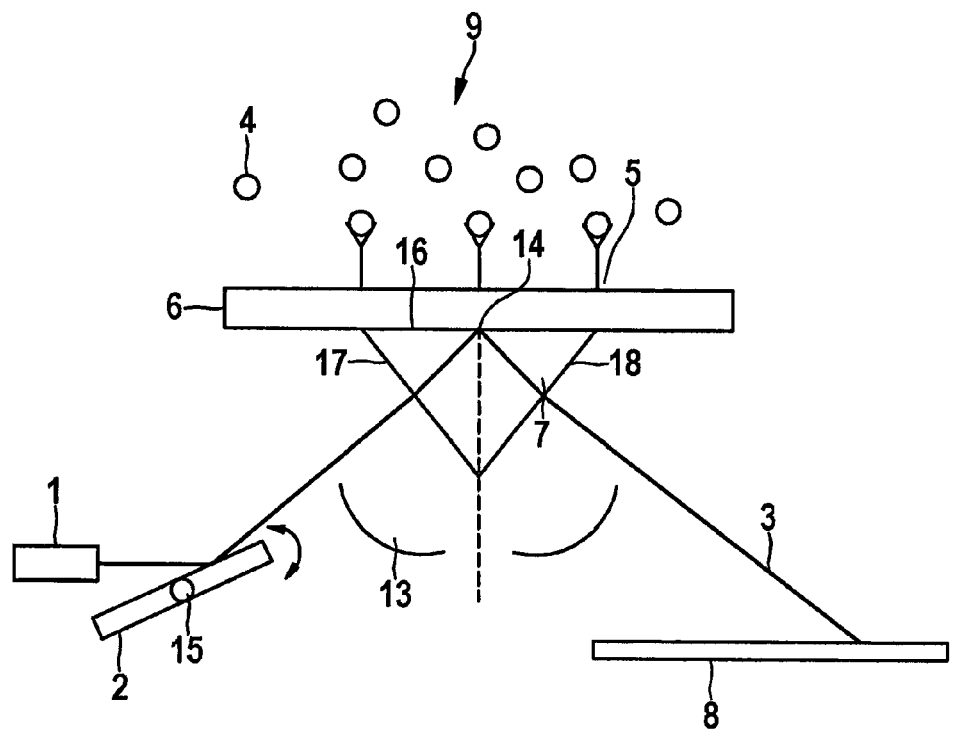
FIG. 1 is a schematic cross section of a plasmonic sensor device with reflection prisms according to a first example embodiment of the present invention.

FIG. 1 shows a schematic cross section of a plasmonic sensor device 9 including a reflection prism 7 according to a first specific embodiment of the present invention.

The device 9 includes a light source 1, a micromirror 2 with an axis of rotation 15, a metallic film 6, a reflection prism 7, a detector 8 as well as linkers 5 that are fastened to metallic film 6, to which analyte molecules 4 are coupled. Light source 1 emits a light beam 3 of coherent light, which is reflected at rotatable micromirror 2 and is guided onto reflection prism 7 at an angle of incidence 13 set by micromirror 2. There, light beam 3 enters via one input surface 17, is reflected at a base surface 16 and exits again at an exit surface 18. After that, light beam 3 strikes detector 8.

Light source 1 can be, for example, a laser, i.e., light beam 3 in FIG. 1 corresponds, in this case, to the laser beam. Using reflection prism 7, which can be made of glass or plastic, for instance, light beam 3 can be coupled to surface plasmons in metallic film 6. For a certain angle of incidence 13, light beam 3 and surface plasmons are in resonance, so that the intensity of light beam 3 is maximally attenuated. The intensity of light beam 3 is measured by detector 8, e.g., a CCD sensor or a CMOS sensor, which determines the light intensity by integration over the active sensor surface. Besides for changing angle of incidence 13, the rotation of micromirror 2 also changes location of incidence 14 of the laser beam. Because of the integration over the extended active area, the intensity measured by detector 8 is, however, independent of location of incidence 14, so that it measures the intensity of light beam 3 as a function of the angle of incidence. In this example embodiment, micromirror 2 is exclusively movable.

All the other components are fixed with respect to one another, so that the plasmonic sensor device is able to be produced in a greatly miniaturized manner. Typical micromirrors 2 (MEMS) are dimensioned in the micrometer range. An extension of a typical plasmonic sensor device 9, as shown in FIG. 1, is a few millimeters perpendicular to metallic film 6. In the width, in the direction of the plane of metallic film 6, plasmonic sensor device 9 extends over a few centimeters, for example.

In an example embodiment, linkers 5 couple the analyte molecules 4 to metallic film 6. Analyte molecules 4, thus coupled, influence the excitation properties of metallic film 6 for surface plasmons, that is, in particular, angle of incidence 13 is displaced at which a minimum intensity of light beam 3 is present. Metallic film 6 can be made of gold, silver or a correspondingly suitable metal, for example.

This example embodiment of plasmonic sensor device 9, as shown in FIG. 1, is exemplary, and different arrangements of the elementary components as well as different embodiments of the components can be provided. For example, according to an alternative example embodiment, the sensor device 9 includes a plurality of micromirrors 2, which, in this context, are able to be rotated or tilted either continuously or in discrete steps. Furthermore, in example embodiment, micromirrors 2 can be provided which are able to be rotated or tilted in various directions about different axes of rotation 15.

Figure 2:
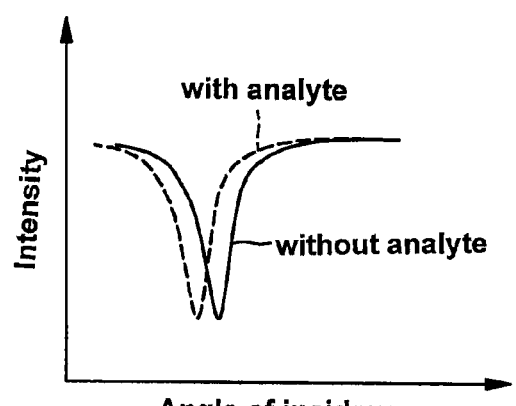
FIG. 2 is a schematic representation of two intensity curves as a function of the angle of incidence, as they appear according to the first example embodiment of the present invention.

FIG. 2 shows, in exemplary fashion, a schematic representation of two intensity curves as a function of angle of incidence 13, according to the example embodiment described above with respect to FIG. 1.

One of the intensity curves corresponds to the case in which analyte molecules 4 are coupled to metallic film 6 via linkers 5, and the other to the case in which no analyte molecules 4 are coupled. FIG. 2 makes clear that the intensity minimum has been shifted for the case in which analyte molecule 4 are coupled to metallic film 6. The change in the intensity minimum illustrated in FIG. 2 should be seen as exemplary. In general, the excitation conditions of surface plasmons in metallic film 6 are influenced by the state of the analyte molecules 4. In principle, the curve of the intensity is a function of the angle of incidence on the construction of the sensor device, particularly on the metal selected and the coupling of the analyte. Such a plasmonic sensor device 9 is suitable for the analysis of the most varied analytes and their properties, and can thus be used in diverse fields, for instance, in the field of medical diagnosis as a portable point-of-care test (POCT). Additional fields of application can be found in pharmaceutical research, for investigating the binding properties of active ingredients, or in biosensor systems. The present invention is suitable for use in liquids and gaseous media, and can thus be used in any case in which low concentrations of substances are to be detected directly on the spot. In particular, because of the great miniaturization of the sensor device, the application outside of laboratories is practicable. Such a plasmonic sensor device can be integrated into cell phones, tablets, etc., for example.

Figure 3:
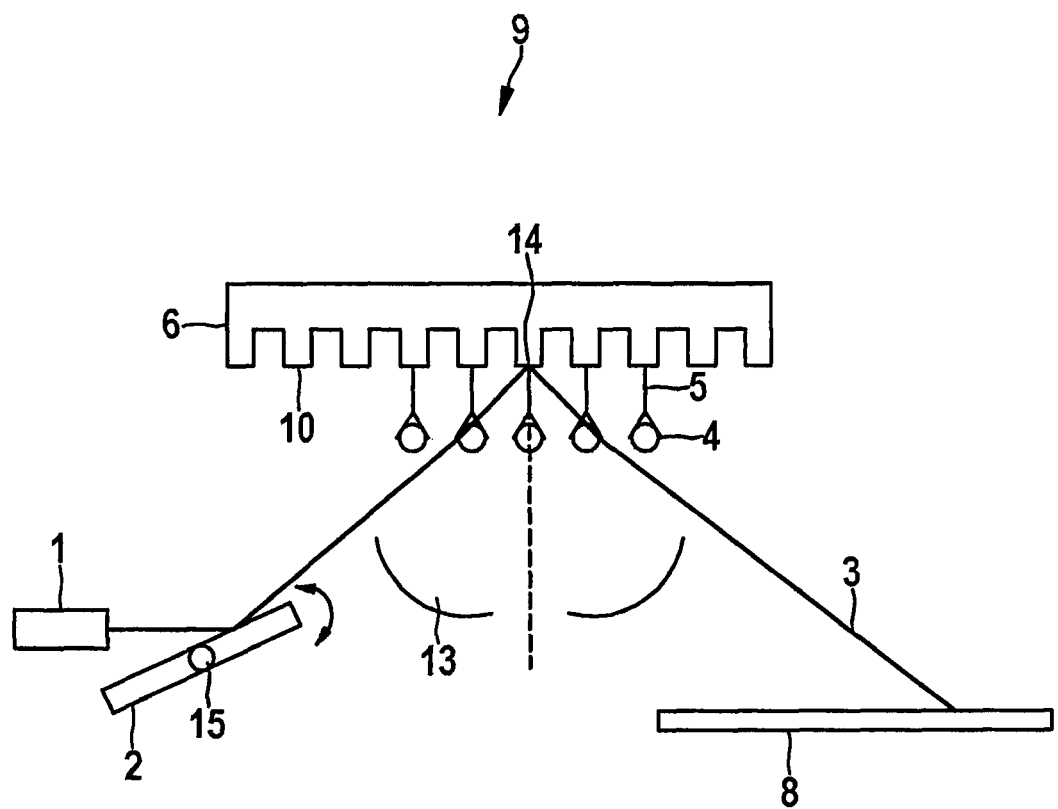
FIG. 3 is a schematic cross section of a plasmonic sensor device with a lattice structure according to a second example embodiment of the present invention.

FIG. 3 shows a schematic cross section of a plasmonic sensor device 9 with a lattice structure 10 according to a second example embodiment of the present invention.

In a manner similar to the first example embodiment in FIG. 1, the sensor device 9 of FIG. 2 includes a light source 1, a micromirror 2 with an axis of rotation 15, a metallic film 6, a detector 8 as well as linkers 5 fastened to metallic film 6, to which analyte molecules 4 are coupled. In contrast to the example embodiment of FIG. 1, linkers 5 and analyte molecules 4 coupled to the linkers 5 are, however, located on the side of metallic film 6 facing detector 8 and light source 1. By contrast to the embodiment in FIG. 1, in this case, in addition, no reflection prism 7 is provided. Rather, metallic film 6 is equipped on the irradiated side with a lattice structure 10. In a manner similar to reflection prism 7 in FIG. 1, lattice structure 10 is also used for coupling coherent light 3 to surface plasmons, but occupies less space than a typical reflection prism 7. The arrangement of components of plasmonic sensor device 9, shown in FIG. 3, is exemplary, and different arrangements of the elementary components as well as different embodiments of the components can be provided. For example, in an example embodiment, the sensor 9 includes a plurality of micromirrors 2, which can be rotated or tilted either continuously or in discrete steps. Beyond that, specific embodiments are also provided in which linkers 5 and analyte molecules 4 are located on the non-irradiated side of metallic film 6, similar to the example embodiment of FIG. 1.

In addition, the manner of functioning of the second example embodiment of FIG. 3 is the same as that of that first example embodiment of FIG. 1. Here, too, light source 1 emits a light beam 3 of coherent light 3, which is reflected by rotatable micromirror 2, conducted onto lattice structure 10 at an angle of incidence 13 that is set by micromirror 2, and reflected from there to strike detector 8, which determines the intensity of light beam 3 as a function of angle of incidence 13.

Consequently, the analysis of an analyte thus includes the following steps. First of all, light source 1 generates coherent light 3. This is reflected at micromirror 2 and guided to the lower side of metallic film 6, that is structured as a lattice. The angle of incidence 13 of light beam 3 on metallic film 6 is varied by rotating or tilting micromirror 2, where, in dependence on angle of incidence 13, surface plasmons in metallic film 6 are excited at the boundary surface between metallic film 6 and analyte molecules 4. The intensity of light beam 3, that is guided onto metallic film 6 and reflected again from there, is measured by detector 8, and, building up on this, the curve of the intensity of light 3 is determined as a function of angle of incidence 13.

Figure 4:
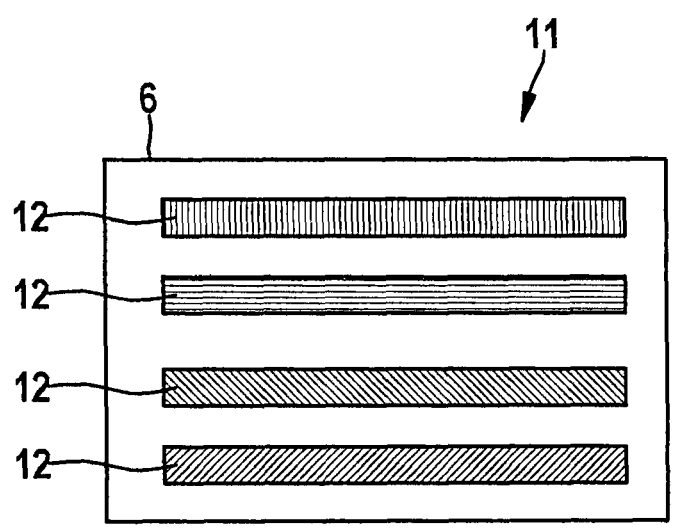
FIG. 4 is a schematic top view on a test strip of a plasmonic sensor device according to an example embodiment of the present invention.

FIG. 4 shows a schematic top view of a test strip 11 of a plasmonic sensor device 9 according to a third example embodiment of the present invention.

The plasmonic sensor device 9 can be, for example, like that of FIG. 3, which provides a lattice structure 10 for coupling light 3 and surface plasmons. In FIG. 4, four adjacent strip-shaped analyte areas 12 of analyte molecules 4 have been applied to a metallic film 6. Each of the four analyte areas 12 can be made up of different analytes. Accordingly, in this case, four different types of linkers 5 are also provided, to which the respective analyte molecules 4 are able to be coupled.

According to the example embodiment shown in FIG. 4, plasmonic sensor device 9 is able to scan metallic film 6 two-dimensionally. This is made possible by rotating a plurality of provided micromirrors 2, or by rotating a single micromirror 2 in various directions. This embodiment is of advantage for a design of the sensor device as a diagnostic unit, for instance, a point-of-care test. In this form, the diagnostic unit can be used similarly to a blood sugar measuring unit or a chip-card reader. Light source 1, micromirror 2 and detector 8 are firmly integrated into the diagnostic unit, in this variant. Test strip 11 is introduced into the unit after the application of one or more substances, and is removed again after the analysis. The two-dimensional scannability of test strip 11 consequently enables testing for various substances, which are coupled to test strip 11 via appropriate linkers 5, for example.

In other embodiments of plasmonic sensor device 9 and of test strip 11, reference structures are provided which can be used, for instance, for an automatic position correction of test strip 11 with respect to other components or are suitable for the automatic alignment of the test strip and the optical components. Furthermore, reserved areas are provided on test strip 11, which can be used for reference measurements.

FIG. 5 shows a schematic cross section of a plasmonic sensor device 9 including reflection prism 7 and three micromirrors 2 in a multi-mirror configuration according to another example embodiment of the present invention.

In principle, the construction and manner of functioning of sensor device 9 can be similar to those of the embodiment of FIG. 1. Sensor device 9 includes a light source 1, micromirrors 2, 2a, 2b with axes of rotation 15, 15a, 15b, a metallic film 6, a reflection prism 7, a detector 8 as well as linkers 5 that are fastened to metallic film 6, to which analyte molecules 4 are coupled. Light source 1 emits a light beam 3 of coherent light, which is reflected at rotatable micromirrors 2, 2a, 2b and is conducted onto reflection prism 7 at an angle of incidence 13 set by micromirrors 2, 2a, 2b. There, light beam 3 enters via the input surface 17, is reflected at a base surface 16 and exits again at an exit surface 18. Thereafter, light beam 3 strikes detector 8, which determines the intensity of light beam 3 as a function of angle of incidence 13. Light beam 3 first strikes a first micromirror 2. The latter guides light beam 3, depending on the angle, to one of the two further micromirrors 2a, 2b, which, in each respective case, then respectively conducts it further to reflection prism 7. The multi-mirror configuration used here creates additional degrees of freedom with respect to the manipulation of angle of incidence 13 and of location of incidence 14 compared to the embodiments with only one micromirror 2, such as that shown in FIG. 1. In this example embodiment of FIG. 5, axes of rotation 15, 15a, 15b of the three micromirrors 2, 2a, 2b are parallel to one another. However, in alternative example embodiments, the axes of rotation 15, 15a, 15b and micromirrors 2, 2a, 2b are aligned in different directions. By a corresponding configuration of micromirrors 2, 2a, 2b it is possible, among other things, that metallic film 6 is not only scanned one-dimensionally in the imaging plane, but particularly also perpendicular to the imaging plane, i.e., two-dimensionally. Thereby, a test strip 11, as shown, for instance, in FIG. 4, can be scanned two-dimensionally, and thus used for diverse purposes. In example embodiments, plasmonic sensor device 9 includes a configuration of N+1 micromirrors 2, 2a, 2b. Because of the miniaturized embodiment of micromirrors 2, 2a, 2b, such embodiments are also able to be designed simply and in a space-saving manner.

What is claimed is:

1. A plasmonic sensor device comprising:
   a light source configured to generate coherent light;
   a metallic film;
   a detector; and
   at least one micromirror that is rotatable about at least one axis of rotation and is arranged to guide the coherent light from the light source to one side of the metallic film from which the coherent light is reflected to the detector, wherein:
   an angle of incidence at which the coherent light is guided to the one side of the metallic film is variable by rotation of the at least one micromirror about the at least one axis of rotation;
   the metallic film is at least partially covered on one side by analyte molecules;
   the detector is configured to determine the intensity of the light, as a function of the angle of incidence; and
   the coherent light generated by the light source is in a state that surface plasmons are excitable in the metallic film in a manner that depends on the angle of incidence; and
   at least one of the following:
   the determination of the intensity of the light includes integrating values over an active surface of the detector, and is independent of location of incidence of the light on the metallic film;
   the plasmonic sensor device further comprises linkers that are located on a side of the metallic film at which the detector is located;
   the at least one micromirror includes a first micromirror that is rotatable about a first one of the at least one axis of rotation and a second micromirror that is rotatable about a second one of the at least one axis of rotation that is not parallel to the first axis of rotation; and
   (a) the at least one micromirror includes the first micromirror, a third micromirror, and a fourth micromirror, (b) the first micromirror is arranged relative to the light source and relative to the third and fourth micromirrors so that the light from the light source impinges on the first micromirror, which is rotatable about its axis of rotation to reflect the impinging light to the third micromirror for a first range of values of the angle of incidence and to the fourth micromirror for a second range of values of the angle of incidence, (c) the third micromirror is rotatable about its axis of rotation to adjust between the values of the first range, and (d) the fourth micromirror is rotatable about its axis of rotation to adjust between values of the second range.

2. The plasmonic sensor device of claim 1, wherein the plasmonic sensor device is configured for the light source, the metallic film, the detector and the at least one axis of rotation of the at least one micromirror to be fixed in their relative positions to one another during operation of the plasmonic sensor device.

3. The plasmonic sensor device of claim 1, wherein the light source is configured to generate a laser beam.

4. The plasmonic sensor device of claim 1, further comprising:
   a reflection prism positioned so that its base surface borders on a side of the metallic film facing away from the analyte molecules and so that the coherent light enters into the prism at an entrance surface of the prism, is reflected at the border between the base surface of the prism and the metallic film, and exits from the prism at an exit surface of the prism, and subsequently strikes the detector.

5. The plasmonic sensor device of claim 1, wherein one side of the metallic film is formed in a lattice structure, and the metallic film is arranged for the lattice structure to reflect the coherent light to the detector.

6. The plasmonic sensor device of claim 1, further comprising linkers that couple the analyte molecules to the metallic film.

7. The plasmonic sensor device of claim 1, wherein the detector is a charge-coupled device (CCD) sensor or a complementary metal-oxide semiconductor (CMOS) sensor.

8. The plasmonic sensor device of claim 1, wherein the metallic film includes at least one of gold and silver.

9. The plasmonic sensor device of claim 1, wherein the plasmonic sensor is configured for the coherent light to scan the metallic film along a first dimension by a first type of rotation of the at least one micromirror and to scan the metallic film along a second dimension by a second type of rotation of the at least one micromirror.

10. The plasmonic sensor device as recited in 9, wherein the metallic film is a test strip, and the plasmonic sensor device further comprises adjacently situated analyte areas with analyte molecules applied onto the test strip.

11. The plasmonic sensor device of claim 9, wherein the at least one micromirror includes the first micromirror that is rotatable about the first one of the at least one axis of rotation as the first type of rotation and the second micromirror that is rotatable about the second one of the at least one axis of rotation that is not parallel to the first axis of rotation as the second type of rotation.

12. The plasmonic sensor device of claim 11, wherein, for each of the scan positions in the second dimension, a combination of values over the active surface of the detector obtained by the scanning along the first dimension while at the respective scan position of the second dimension is used for the measuring, by the detector, of a respective intensity of the coherent light reflected to the detector.

13. The plasmonic sensor device of claim 1, wherein:
the at least one micromirror includes a plurality of micromirrors that are:
rotatable about respective axes of rotation; and
arranged for guiding the coherent light via multiple reflections by the plurality of micromirrors to strike at an angle of incidence onto a location of incidence on one side of the metallic film; and
the angle of incidence and the location of incidence are variable by the respective rotations of the plurality of micromirrors about their respective axes of rotation.

14. The plasmonic sensor device of claim 1, wherein the determination of the intensity of the light includes the integrating of values over an active surface of the detector, and is independent of location of incidence of the light on the metallic film.

15. The plasmonic sensor device of claim 1, wherein the plasmonic sensor device further comprises the linkers that are located on the side of the metallic film at which the detector is located.

16. The plasmonic sensor device of claim 1, wherein the at least one micromirror includes the first micromirror that is rotatable about the first one of the at least one axis of rotation and the second micromirror that is rotatable about the second one of the at least one axis of rotation that is not parallel to the first axis of rotation.

17. The plasmonic sensor device of claim 1, wherein (a) the at least one micromirror includes the first micromirror, the third micromirror, and the fourth micromirror, (b) the first micromirror is arranged relative to the light source and relative to the third and fourth micromirrors so that the light from the light source impinges on the first micromirror, which is rotatable about its axis of rotation to reflect the impinging light to the third micromirror for the first range of values of the angle of incidence and to the fourth micromirror for the second range of values of the angle of incidence, (c) the third micromirror is rotatable about its axis of rotation to adjust between the values of the first range, and (d) the fourth micromirror is rotatable about its axis of rotation to adjust between values of the second range.

18. A method for surface plasmon resonance spectroscopy using a plasmonic sensor device, wherein the plasmonic sensor device includes (a) a light source configured to generate coherent light, (b) a metallic film, (c) a detector, and (d) a micromirror that is rotatable about an axis of rotation and is arranged to guide the coherent light from the light source to one side of the metallic film from which the coherent light is reflected to the detector, an angle of incidence at which the coherent light is guided to the one side of the metallic film being variable by rotation of the micromirror about the axis of rotation, and the metallic film being at least partially covered on one side by analyte molecules, the method comprising:
varying the angle of incidence of the coherent light on the metallic film by rotating the micromirror, wherein surface plasmons are excitable in the metallic film in a manner that depends on the angle of incidence; and
measuring, by the detector, the intensity of the coherent light reflected to the detector as a function of the angle of incidence;
wherein at least one of the following:
the measuring of the intensity of the light includes integrating values over an active surface of the detector, and is independent of location of incidence of the light on the metallic film;
the plasmonic sensor device further comprises linkers that are located on a side of the metallic film at which the detector is located;
the micromirror includes a first micromirror that is rotatable about a first one of the at least one axis of rotation and a second micromirror that is rotatable about a second one of the at least one axis of rotation that is not parallel to the first axis of rotation; and
(a) the micromirror includes the first micromirror, a third micromirror, and a fourth micromirror, (b) the first micromirror is arranged relative to the light source and relative to the third and fourth micromirrors so that the light from the light source impinges on the first micromirror, which is rotatable about its axis of rotation to reflect the impinging light to the third micromirror for a first range of values of the angle of incidence and to the fourth micromirror for a second range of values of the angle of incidence, (c) the third micromirror is rotatable about its axis of rotation to adjust between the values of the first range, and (d) the fourth micromirror is rotatable about its axis of rotation to adjust between values of the second range.

19. The method of claim 18, further comprising:
scanning the metallic film by rotating the micromirror and thereby varying a location of incidence of the coherent light on the metallic film.

* * * * *